United States Patent
Pascale

(10) Patent No.: US 11,693,228 B2
(45) Date of Patent: **\*Jul. 4, 2023**

(54) DEVICE FOR HEAT DISSIPATION FROM AN ENDOSCOPIC ILLUMINATION APPARATUS

(71) Applicant: KARL STORZ SE & CO. KG, Tuttlingen (DE)

(72) Inventor: Costantino Pascale, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 207 days.

This patent is subject to a terminal disclaimer.

(21) Appl. No.: 17/208,077

(22) Filed: Mar. 22, 2021

(65) Prior Publication Data

US 2021/0208385 A1    Jul. 8, 2021

Related U.S. Application Data

(63) Continuation of application No. 16/891,551, filed on Jun. 3, 2020, now Pat. No. 10,983,332.

(30) Foreign Application Priority Data

Jun. 3, 2019   (DE) .................. 10 2019 114 885.5

(51) Int. Cl.
  *G02B 23/24*   (2006.01)
  *F21V 29/60*   (2015.01)
  (Continued)

(52) U.S. Cl.
  CPC .......... *G02B 23/2476* (2013.01); *F21V 29/60* (2015.01); *F21V 29/89* (2015.01);
  (Continued)

(58) Field of Classification Search
  CPC . G02B 23/2476; G02B 23/2461; F21V 29/60; F21V 29/89; F28D 15/0266;
  (Continued)

(56) References Cited

U.S. PATENT DOCUMENTS 5,099,399 A   3/1992   Miller et al.
7,384,151 B2  6/2008   Seki
(Continued)

FOREIGN PATENT DOCUMENTS

CN       1854833 A   11/2006
CN    101334150 A   12/2008
(Continued)

OTHER PUBLICATIONS

First Office Action (Including Translation) for corresponding Chinese Patent Application No. 202010473819.5, dated Mar. 30, 2021.
(Continued)

*Primary Examiner* — Anne M Hines
(74) *Attorney, Agent, or Firm* — Jason H. Vick; Sheridan Ross, PC

(57) ABSTRACT

Device for an endoscopic illumination apparatus comprising a heat pipe having a first end region and a second end region; a first heat source; a heat dissipation element for dissipating thermal energy from said first heat source; a heat sink spaced apart from the first heat source; and a clamping element, wherein the clamping element is reversibly detachably mounted on the heat dissipation element such that the first end region of the heat pipe is held between the heat dissipation element and the clamping element, wherein the heat pipe is adapted to conduct the thermal energy of the heat source to the heat sink, wherein the second end region of the heat pipe is spaced apart from the first end region, and wherein the second end region ends in the heat sink.

23 Claims, 7 Drawing Sheets

(51) Int. Cl.
  *F21V 29/89* (2015.01)
  *F28D 15/02* (2006.01)
  *A61B 1/12* (2006.01)
  *F28D 21/00* (2006.01)

(52) U.S. Cl.
  CPC ..... *F28D 15/0266* (2013.01); *F28D 15/0275* (2013.01); *G02B 23/2461* (2013.01); *A61B 1/128* (2013.01); *F28D 2021/005* (2013.01); *F28D 2021/0029* (2013.01)

(58) Field of Classification Search
  CPC ......... F28D 15/0275; F28D 2021/0029; F28D 2021/005
  See application file for complete search history.

(56) References Cited

U.S. PATENT DOCUMENTS

| | | | |
|---|---|---|---|
| 8,696,554 | B2 | 4/2014 | Omori |
| 10,085,630 | B2 | 10/2018 | Shirota et al. |
| 10,092,174 | B2 | 10/2018 | Shirota et al. |
| 2006/0268552 | A1 | 11/2006 | Irion et al. |
| 2008/0117597 | A1 | 5/2008 | Zhou et al. |
| 2016/0353984 | A1 | 12/2016 | Shirota et al. |
| 2016/0367119 | A1* | 12/2016 | Ouyang .............. A61B 1/0676 |
| 2019/0021583 | A1 | 1/2019 | Yoshida et al. |
| 2019/0056583 | A1 | 2/2019 | Kuhn et al. |
| 2020/0379247 | A1 | 12/2020 | Miller et al. |

FOREIGN PATENT DOCUMENTS

| | | |
|---|---|---|
| CN | 102261580 A | 11/2011 |
| CN | 105979851 A | 9/2016 |
| DE | 102007038909 A1 | 2/2009 |
| DE | 102007038911 A1 | 2/2009 |
| DE | 102017118941 B3 | 8/2018 |
| DE | 102017007198 A1 | 2/2019 |
| EP | 1731862 A1 | 12/2006 |
| JP | 2014-045820 A | 3/2014 |

OTHER PUBLICATIONS

German Search Report for German Application No. 10 2019 114 885.5, dated Mar. 2, 2020.
European Search Report for corresponding European Application No. 20175838.0, dated Oct. 9, 2020.
Office Action for U.S. Appl. No. 16/891,551, dated Nov. 27, 2020.
Notice of Allowance for U.S. Appl. No. 16/891,551, dated Dec. 30, 2020.
Office Action for corresponding European Application No. 20175838.0, dated Aug. 26, 2021.

* cited by examiner

DEVICE FOR HEAT DISSIPATION FROM AN ENDOSCOPIC ILLUMINATION APPARATUS

CROSS REFERENCE TO RELATED APPLICATIONS

This application is a continuation of U.S. patent application Ser. No. 16/891,551, filed Jun. 3, 2020, now U.S. Pat. No. 10,983,332, which claims priority from German patent application 10 2019 114 885.5, filed on Jun. 3, 2019. The entire contents of these priority applications are incorporated herein by reference.

BACKGROUND OF THE DISCLOSURE

The present disclosure relates to a device for an endoscopic illumination apparatus and an endoscopic illumination apparatus with said device.

Endoscopes are used both in the technical field and in the medical field and are particularly suitable for inspection of areas which are difficult to access and therefore, are not observable with the naked eye. For example, in the technical field, endoscopes are used for work in cavities in machines, engines, turbines and reaction chambers, etc. which cannot be inspected with the naked eye.

In medical endoscopy, endoscopes are used in minimally invasive surgery, where required in combination with surgical instruments, for examination purposes or for operations under visual control or for the application of diagnostic or therapeutic light.

On the one hand, endoscopes comprise an imaging system that serves to receive observation light from the observation room or operating room and to transmit image information from distal to proximal.

The imaging system may be an optical image transmission system comprising an objective in the distal end of a shaft and a lens system which is adjacent to said objective. The lens system may be, for example, a relay system or may comprise an ordered fiber bundle and a proximal ocular. It is also possible that a camera is connectable.

Another component of endoscopes is an illumination system which serves to transmit light from proximal to distal in order to illuminate the observation room or examination room with light. Conventional high-performance light-emitting diodes (LEDs) are used for illumination. This technology particularly offers the advantage that, in comparison to xenon technology, it enables an almost constant light performance over a long lifetime and also guarantees a constant quality of illumination of the light sources. A further advantage of LED technology is that extended diagnostics such as ICG (indocyanine green) and PDD (photodynamic diagnostics) can be realized by combining LEDs of different spectra.

In order to guarantee the high performance and long lifetime of LED technology, a sufficiently dimensioned cooling management is essential, since the applied LEDs continue to represent heat sources despite their high efficiency due to their high light performance.

The rejected heat produced by the LEDs or light sources can, for example, be dissipated into an endoscope housing (see e.g. U.S. Pat. No. 8,696,554 B2). However, this solution of heat dissipation may lead to a heat accumulation, which may cause overheating of the LEDs and their peripherals. It is therefore advantageous if the generated heat is conducted from its point of origin to a heat sink (e.g. in the form of a cooling body). In the simplest case, this may be achieved by providing flow passages within the housing of the endoscope, through which an air flow is initiated, for example, by a fan (see U.S. Pat. No. 5,099,399 A). This solution is disadvantageous, however, since the flow passages within the housing limit the freedom of design of the housing.

A possibility to increase the freedom of structural design and heat dissipation performance is to separate the heat source and heat sink by using so-called heat pipes. These heat pipes, which are also called heat conduction tubes, allow, for example, a fluidically optimal positioning of the heat sink within the endoscopic illumination apparatus and serve for heat exchange between the heat source and the heat sink.

The connection of heat pipes to the heat sources may be carried out, for example, by soldering or welding. In addition, the heat pipes may also be integrally connected to the heat source. An example of heat dissipation using heat pipes can be found in JP 2014-045820 A and EP 1 731 862 A1. JP 2014-045820 A and EP 1 731 862 A1 each relate to a design in which the heat pipe is integrally connected to the heat source.

SUMMARY OF THE DISCLOSURE

It is an object to further develop a device for heat dissipation from an endoscopic illumination apparatus in such a way that a higher degree of freedom in structural design and/or an increase in the heat dissipation capacity may be reached.

The object is solved by device for an endoscopic illumination apparatus comprising a heat pipe having a first end region and a second end region, a first heat source, a heat dissipation element for dissipating thermal energy from said first heat source, a heat sink spaced apart from the first heat source, and a clamping element. The clamping element is reversibly detachably mounted on the heat dissipation element such that the first end region of the heat pipe is held between the heat dissipation element and the clamping element. The heat pipe is adapted to conduct the thermal energy of the heat source to the heat sink. The second end region of the heat pipe is spaced apart from the first end region, and the second end region ends in the heat sink.

Due to the way the heat pipe functions, a temperature gradient occurs between the hot end of the heat pipe, which is located at the heat source, and the cold end of the heat pipe, which is located in the heat sink, during the heat dissipation of the heat generated by the heat source. This temperature gradient leads to different, material-related temperature expansions along the heat pipe.

The inventors have recognized that, due to the rigid attachment of the respective ends of the heat pipe to the heat source or heat sink, resulting internal stresses may be transferred to other components of the endoscopic illumination apparatus. This may, for example, impair accuracy of image acquisition.

It was also recognized that due to the manufacturing tolerances of the heat pipes positioning of the heat sources (in particular LEDs) relative to the heat pipes may be highly demanding. Also, the positioning may be associated with a high degree of adjustment and assembly effort, since the arrangement of the heat pipes is limited, for example, due to a predetermined position and orientation of the imaging system, in particular the lens system and the objective (e.g., a glass rod).

In this context, the inventors have recognized that, for example, parallel heat dissipation (a straight-line course of the heat pipes) may be difficult to realize and that the heat pipes for placement in the housing of the endoscopic lighting apparatus may generally follow a curved course, which may increase the consequences of distortion or deformation due to internal stress.

One of the advantages of the embodiment may be, in contrast to the prior art, the heat pipe may not be permanently connected to the heat source or the heat dissipation element of the heat source but may be reversibly detachably mounted. By arranging the heat pipe between the heat dissipation element and the clamping element, i.e. by clamping or restraining the heat pipe, it may not be fixedly connected with one end to the heat dissipation element, but may only be clamped in place by means of a force fit. This means that in particular the aforementioned internal stresses may no longer be transferred to the components surrounding the heat pipe.

The surface area available for heat transfer may also be increased by locating the heat pipe between the heat dissipation element and the clamping element, since the heat pipe is enclosed by the heat dissipation element and the clamping element in the first end region. This means that the entire outer surface of the first end region of the heat pipe may be available for heat transfer.

In addition, this attachment of the heat pipe may significantly increase the freedom of structural design, since both the heat dissipation element and the clamping element may be adapted to a particular course of the heat pipe. Thus, a modular arrangement of the heat pipe may be possible. In addition, for example, the aforementioned manufacturing tolerances of the heat pipe may be compensated for in the overall system, which in turn may be reflected in increased freedom of structural design.

The embodiment may offer a suitable option, in particular for retrofitting, i.e. for the subsequent modification of individual components, since the clamping mechanism may be reversibly detachable. This means, for example, that the heat pipe may be easily replaced. In some exemplary embodiments, the heat pipe may also be soldered to the heat sink, wherein in such a case, the heat sink and heat pipe may be replaced together in a retrofit.

In other words, the heat dissipation element may be mounted in a precise position on the heat source, which may be, for example, a component of an optical unit of an endoscopic illumination apparatus. In contrast to the state of the art, however, the heat pipe may not be connected by soldering or welding, i.e. not by a form-fitting, nonreversible process, but by using the clamping element.

The terms "heat dissipation element" and "clamping element" in this case may be understood, in some exemplary embodiments, to mean a plate- or cuboid-shaped body, e.g. made of a metal or an alloy. In an exemplary embodiment, the body may comprise one or more recesses. In some exemplary embodiments, the recesses may be adapted to accommodate the heat pipe at least partially. A rod-shaped end section of the heat pipe may, for example, be accommodated proportionally in a recess of the heat dissipation element and proportionally in a recess of the clamping element corresponding to the recess of the heat dissipation element in the mold, such that the end region of the heat pipe may be, in an exemplary embodiment, completely enclosed by both recesses.

The term "heat pipe" in this case means a heat conducting pipe. Heat pipes, in some exemplary embodiments, may include metal vessels of elongated shape which may have a hermetically sealed volume. The volume may be filled with a working medium (e.g. water or ammonia) which may fill the volume to a small extent in the liquid state and to a relatively larger extent in the gaseous state. The working medium may be vaporized in the area of the heat source while the heat pipe is in use. The working medium condenses again in the area of the heat sink and returns to the area of the heat conduction tube on the heat source side, driven by capillary forces.

Furthermore, the term "heat pipe" may also be used to describe a metal rod made of solid material, e.g. with a round or rectangular cross section, in which heat transport takes place by conduction, i.e. by the transfer of kinetic energy between adjacent atoms of the metal rod without material transport.

According to an exemplary embodiment, the heat source is a light source.

The term "light source" may be, in some exemplary embodiments, understood to mean a light-emitting diode (short: LED). In principle, however, a xenon light may also be used as a light source, wherein light-emitting diodes may be used due to their longer lifetime in comparison to xenon lights as well as due to their higher efficiency.

According to another exemplary embodiment, the clamping element is detachably screwed, pinned or bolted to the heat dissipation element.

This embodiment may have the advantage that the clamping element may be easily mounted to the heat dissipation element but may also be easily removed from it. For some exemplary embodiments, the clamping element may be connected to the heat dissipation element via one or more screws or bolts. When pinning (i.e. inserting bolts for fastening), in some exemplary embodiments, so-called safety pins may be used to prevent the pins from being pulled out.

According to another exemplary embodiment, the heat pipe, the heat dissipation element and the clamping element are each made of a thermally conductive material.

The thermally conductive material may be adapted such that the heat generated at the heat source or by the light-emitting diode may substantially be completely transferred from the heat dissipation element to the heat pipe without any heat build-up due to heat transfer inhibiting properties, respectively. Here, the heat transfer between the heat dissipation element and the heat pipe may take place via a common interface. This means that, in some exemplary embodiments, there may be no air gap between the heat dissipation element and the heat pipe, which air gap has an insulating effect for heat transport. In an exemplary embodiment, the heat pipe and the heat dissipation element may be made of copper, the clamping element may be made of aluminum. However, in some exemplary embodiments, the heat pipe, the heat dissipation element and the clamping element may all be made of the same thermally conductive material.

According to another exemplary embodiment, the thermally conductive material comprises aluminum or copper or is aluminum or copper.

Here, both thermally conductive materials that only contain copper and/or aluminum, for example, as an alloy component, as well as those that consist of pure copper or aluminum are included. In this context, it does not depend on the proportion of copper and/or aluminum in the thermally conductive material as long as the thermal conductivity of the thermally conductive material is expected to be substantially (±20%) equal to the thermal conductivity of copper or aluminum.

According to a further embodiment, a heat-conducting paste for thermal coupling is applied between a surface of the heat dissipation element, a surface of the first end region of the heat pipe and a surface of the clamping element.

One advantage of the additionally applied heat-conducting paste may be that the thermal conductivity may thereby be increased in the region of the boundary layer, i.e. in the region where the respective surfaces of the heat dissipation element, the first end region of the heat pipe and the clamping element get into contact with each other. For example, the heat-conducting paste may also be applied only in the contact region of the surface of the heat dissipation element and the surface of the first end region of the heat pipe, since the majority of the heat transfer of the heat to be dissipated takes place in this contact region. Instead of heat-conducting paste, a heat-conducting pad may also be used. Alternatively or in addition, a heat-conducting paste or pad may be placed between the light source (i.e. a LED) and the heat dissipation element.

The surface may understood to be, for example, the surface of a wall or wall section of the heat dissipation element, of the first end region of the heat pipe or of the clamping element, respectively.

The first end region of the heat pipe may be the region that is clamped between the heat dissipation element and the clamping element in the assembled state.

According to another exemplary embodiment, the device further comprises a second heat pipe, a second heat dissipating element, a second clamping element, and a second heat source, the second heat pipe having a first end region and a second end region, wherein the second heat dissipation element is adapted to dissipate thermal energy from the second heat source. The second clamping element is reversibly detachably mounted on the second heat dissipation element such that the first end region of the second heat pipe is held between the second heat dissipation element and the second clamping element. The second heat pipe is adapted to conduct the thermal energy of the second heat source to the heat sink, wherein the second end region of the second heat pipe is spaced apart from the first end region, and wherein the second heat pipe ends in the heat sink.

This embodiment includes in particular a design in which, for example, two light-emitting diodes are used as light sources, each of which in turn produces rejected heat. In this embodiment, each heat source has its own heat dissipation element. The heat of the respective heat source is conducted via the respective heat pipe to the heat sink, which may be a common heat sink, wherein embodiments are also conceivable where the second heat pipe ends in a second heat sink which is arranged separately from the first heat sink. This embodiment may have the advantage that the flexibility of the arrangement of the first and second heat source and thus the flexibility of the device is increased.

According to another embodiment, the device further comprises a second heat pipe, a second clamping element, and a second heat source, the second heat pipe having a first end region and a second end region, wherein the heat dissipation element is further adapted to dissipate thermal energy from the second heat source. The second clamping element is reversibly releasably mounted on the heat dissipation element such that the first end region of the second heat pipe is held between the heat dissipation element and the second clamping element. The second heat pipe is adapted to conduct the thermal energy of the second heat source to the heat sink, wherein the second end region of the second heat pipe is spaced apart from the first end region, and wherein the second heat pipe ends in the heat sink.

This embodiment may have the advantage that a common heat dissipation element can be used, especially when the two heat sources are arranged adjacent to one another. The two heat pipes are therefore mounted with two clamping elements on only one common heat dissipation element, which, in some exemplary embodiments, is adapted such that it can absorb the heat generated in the two heat sources relatively close to its respective point of origin.

In another exemplary embodiment, the second heat source is a second light source. For the second light source, the aforementioned with respect to the first light source applies accordingly.

In a further exemplary embodiment, the endoscopic illumination apparatus further comprises a cooling body forming the heat sink of the device and, in some exemplary embodiments, comprises a plurality of cooling fins. In addition, the endoscopic illumination apparatus, in some exemplary embodiments, comprises a fan adapted to force an air flow in a direction towards the heat sink or in a direction away from the heat sink.

In the present case, the term "cooling body" may be understood to mean, for example, a block-like metallic body which is shaped in such a way that its heat-emitting surface is enlarged in comparison with a continuous metallic cuboid. The increase in surface area may be achieved, for example, by a large number of notches and/or bulges.

The fan or blower, in some exemplary embodiments, may be adapted to accelerate stationary ambient air by rotating the rotor blades in such a way that a forced air flow is created, which may, in some exemplary embodiments, flow directly against the heat sink or draws the air surrounding the heat sink directly away from it. In some exemplary embodiments, the fan is located at or near the heat sink.

It is noted that the previously indicated features and the features that will be explained in the following cannot only be provided in the explicitly disclosed combination but also in other combinations or even in isolation without departing from the scope of and spirit of the present disclosure.

BRIEF DESCRIPTION OF THE DRAWINGS

Embodiments are disclosed in the drawings and are explained in the following description. In the figures.

DESCRIPTION OF EXEMPLARY EMBODIMENTS

Figure 1:
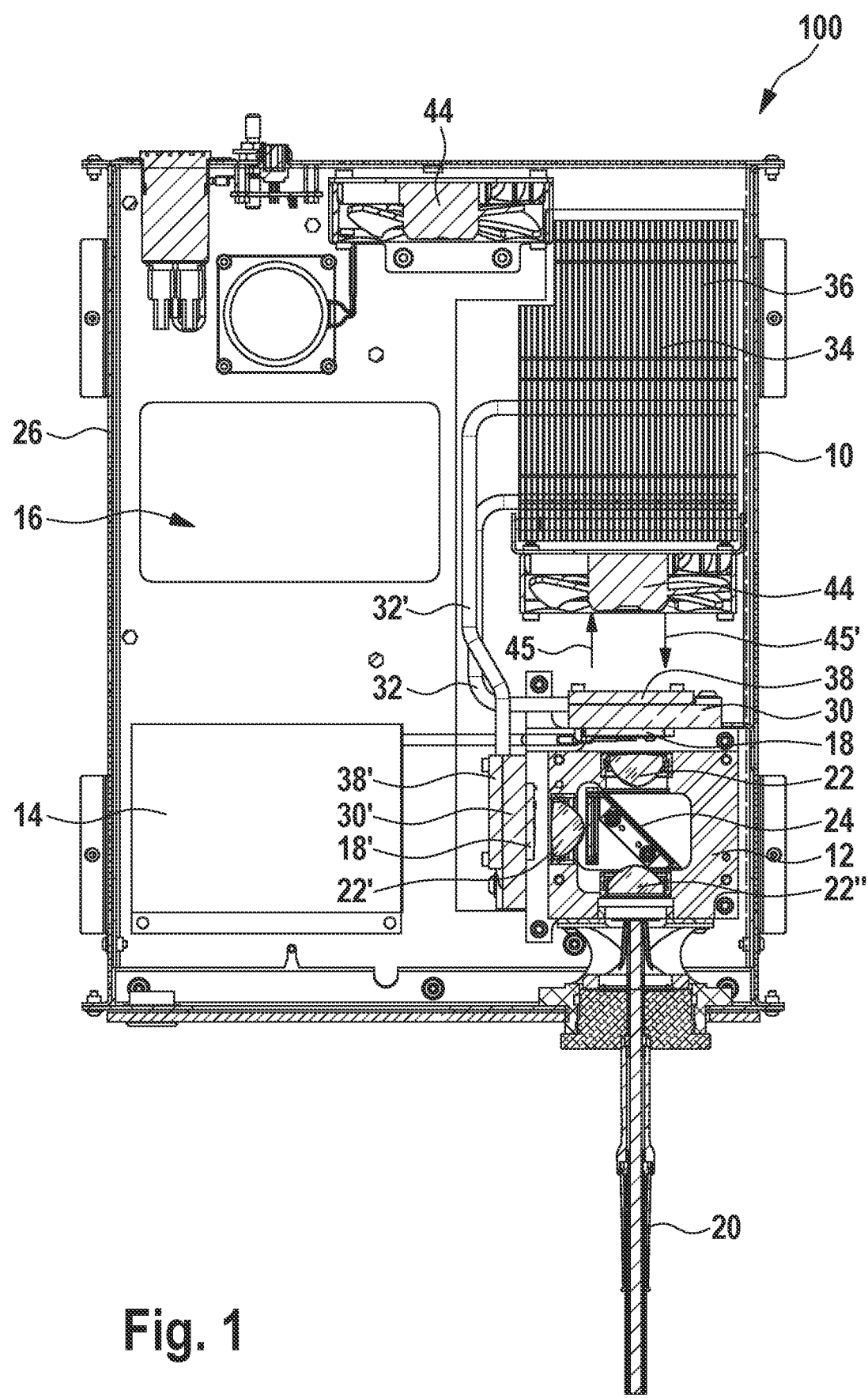
FIG. 1 is a top view of an endoscopic lighting apparatus with a refinement of the device.

FIG. 1 shows an endoscopic lighting apparatus with a refinement of the device. The endoscopic lighting apparatus is marked in its entirety with the reference number 100, the device with the reference number 10.

In the refinement shown in FIG. 1, the endoscopic illuminating apparatus 100 comprises the device 10, an optical unit 12, a light source driver board 14 and a power supply unit 16 as main components.

A main board is not shown in the sectional view. The main board may be arranged above the power supply unit 16 and may be seen as the control and evaluation unit of the endoscopic illumination apparatus 100. The power supply unit 16 is adapted to supply the endoscopic illumination apparatus 100 and all its components with electrical energy and comprises, for example, a power of up to 150 W with convection cooling, up to 250 W with conduction cooling and up to 550 W with forced cooling.

The optical unit 12 forms the "core" of the endoscopic illumination apparatus 100 and is adapted to focus light emitted by one or more light sources 18, 18' in such a way that the light is introduced as a concentrated light beam into a light guide 20. Here, the optical unit 12 comprises a basic carrier, which may be, for example, made of aluminum. The first and the second light source 18, 18' are plate-shaped light emitting diodes (e.g. in SMD design). The first and second light source 18, 18' are arranged orthogonally to each other. The first light source 18 is arranged opposite the light guide 20, thus facing the latter.

An optical lens 22 (e.g. a collimator optic) is arranged in front of the first and the second light source 18, 18' and in front of the light guide 20, respectively. The lenses 22 may each be held by a lens holder. The lenses 22 are adapted to align or collimate the light generated by the light sources 18, 18'. The optics 22, 22', 22" connected in front of the first and the second light source 18, 18' focus the generated light on a center of a beam splitter 24. The beam splitter 24 is aligned with respect to the two light sources 18, 18' in such a way that it has a 45° position to each of the two light sources 18, 18'.

The beam splitter 24 is adapted to allow the light from the first light source 18 to pass in a straight line, i.e. without deflection, in the direction of the light guide 20, whereas the beam splitter 24 deflects the light originating from the second light source 18' and collimated by the lens 22' by 90° in the direction of the light guide 20. For this purpose, the beam splitter 24 may, for example, have a partially transmissive coating. The light directed into the light guide 20 is collimated again by the lens 22" before entering the light guide 20. The light collimated by the optical unit 12 in this way can be directed through the light guide 20 to a location to be illuminated by the endoscopic illumination apparatus 100.

To control the light sources 18, 18' during operation, the main board may be supplied with electrical energy by means of the power supply unit 16. Control signals for controlling the light sources 18, 18' may be transmitted from the main board to the respective light source driver board. The light source driver board(s) transforms the power to the respective light source 18, 18'. Although the light sources 18, 18' are high-power light-emitting diodes having a high efficiency, during operation of the two light sources 18, 18' rejected heat is generated which, if not dissipated, can lead to a heat accumulation, e.g. in a housing 26 of the endoscopic illumination apparatus 100. The light sources 18, 18' are therefore heat sources 28, 28', wherein the first light source 18 represents a first heat source 28 and the second light source 18' represents a second heat source 28'. In other configurations also only one heat source 28, 28' or one light source 18, 18' may be present.

To dissipate the thermal energy (or rejected heat) generated at the light sources 18, 18', the device 10 comprises a heat dissipation element 30, 30'. In the present case, the device 10 comprises a first heat dissipation element 30 and a second heat dissipation element 30'. The first heat dissipation element 30 is arranged in a direct periphery of the first heat source 28. The second heat dissipation element 30' is arranged in a direct periphery of the second heat source 28'. The light sources 18, 18' may be mounted on the heat dissipation elements 30, 30'. The heat dissipation elements 30, 30' may be connected to the base carrier of the optical unit 12. In other refinements, which are not shown here, only one heat dissipation element 30, 30' can be used, which is further adapted to dissipate the thermal energy of both heat sources 28, 28'. Such a heat dissipation element 30, 30' may, for example, have an L-shape and thus may be adapted to dissipate the thermal energy from both the first and the second heat source 28, 28'. In a further refinement, three or more heat dissipation elements may also be used, wherein the number of heat dissipation elements can be determined, for example, on the basis of the power loss to be dissipated.

The thermal energy of the first heat source 28 dissipated by the first heat dissipation element 30 is dissipated via a first heat pipe 32 to a heat sink 34 which is at a distance from the first heat source 28. In the present case, the device also comprises a second heat pipe 32'. The first and second heat pipe 32, 32' may each comprise a plurality (>2) of heat pipes. The thermal energy of the second heat source 28' dissipated by the second heat dissipation element 30' is dissipated via the second heat pipe 32' to the heat sink 34 which is at a distance from the second heat source 28. In the present case, the heat sink 34 is formed by a cooling body 36, which may be a laminated aluminum cooling body. In other refinements, however, the cooling body 36 may also be a different type of cooling body (e.g. with a finned structure, an extruded cooling body or a forged cooling body) or may be composed of several cooling bodies lined up or arranged side by side. In principle, it is also possible that the device 10 comprises two separate heat sinks 34.

In the present case, the first and second heat pipe 32, 32' are tubular or rod-shaped and differ in their respective shape. Here the shape, i.e. the course of the tube, of the respective heat pipe 32, 32' is adapted to the position and positioning of the heat dissipation elements 30, 30'. The heat pipes 32, 32', for example, comprise several straight pipe sections as well as several bends and/or bent pipe sections.

The first heat pipe 32 is reversibly detachably mounted on the first heat dissipation element 30 by means of a first clamping element 38 such that a first end region 40 of the first heat pipe 32 is held between the first heat dissipation element 30 and the first clamping element 38. The second heat pipe 32' may be reversibly detachably mounted on the second heat dissipation element 30' by means of a second clamping element 38' such that a first end region 40' of the second heat pipe 38' is held between the second heat dissipation element 30' and the second clamping element 38'. In a case where there is only one heat dissipation element 30, 30', where both clamping elements 38, 38' may be mounted on the single heat dissipation element 30, 30'.

In the present case, the first and the second heat pipe 38, 38' are adapted to conduct the thermal energy of the first and second heat source 28, 28' to the heat sink 34, which is spaced apart from the heat sources 28, 28'. A second end region 42 of the first heat pipe 32, which is spaced apart from the first end region 40, ends in the heat sink 34, and a second end region 42' of the second heat pipe 32', spaced apart from the first end region 40' of the second heat pipe 32', and may also end in the heat sink 34 (see in particular FIG. 5).

The endoscopic lighting apparatus 100 of FIG. 1 comprises, in addition to the cooling body 36 forming the heat sink 34, a fan 44, which is adapted to force an air flow into the direction 45 of the heat sink 36 or in the opposite direction 45' away from said heat sink 36. In the present case, the fan 44 generates an air flow pointing into the direction 45 of the heat sink 36. In other refinements, a suction fan 44 may also be used, which sucks the air in the opposite direction 45' away from heat sink 36. In addition, in FIG. 1 another fan 44 is arranged in the periphery of the power supply unit 16 and is adapted to suck the thermal energy emitted by the power supply unit 16, the light source driver board 14 and the, in some exemplary embodiments, overlying main board (not shown), out of the housing 26. In a further refinement, the fan 44 can also be arranged on heat sink 36 such that air can be sucked through the heat sink.

Figure 2:
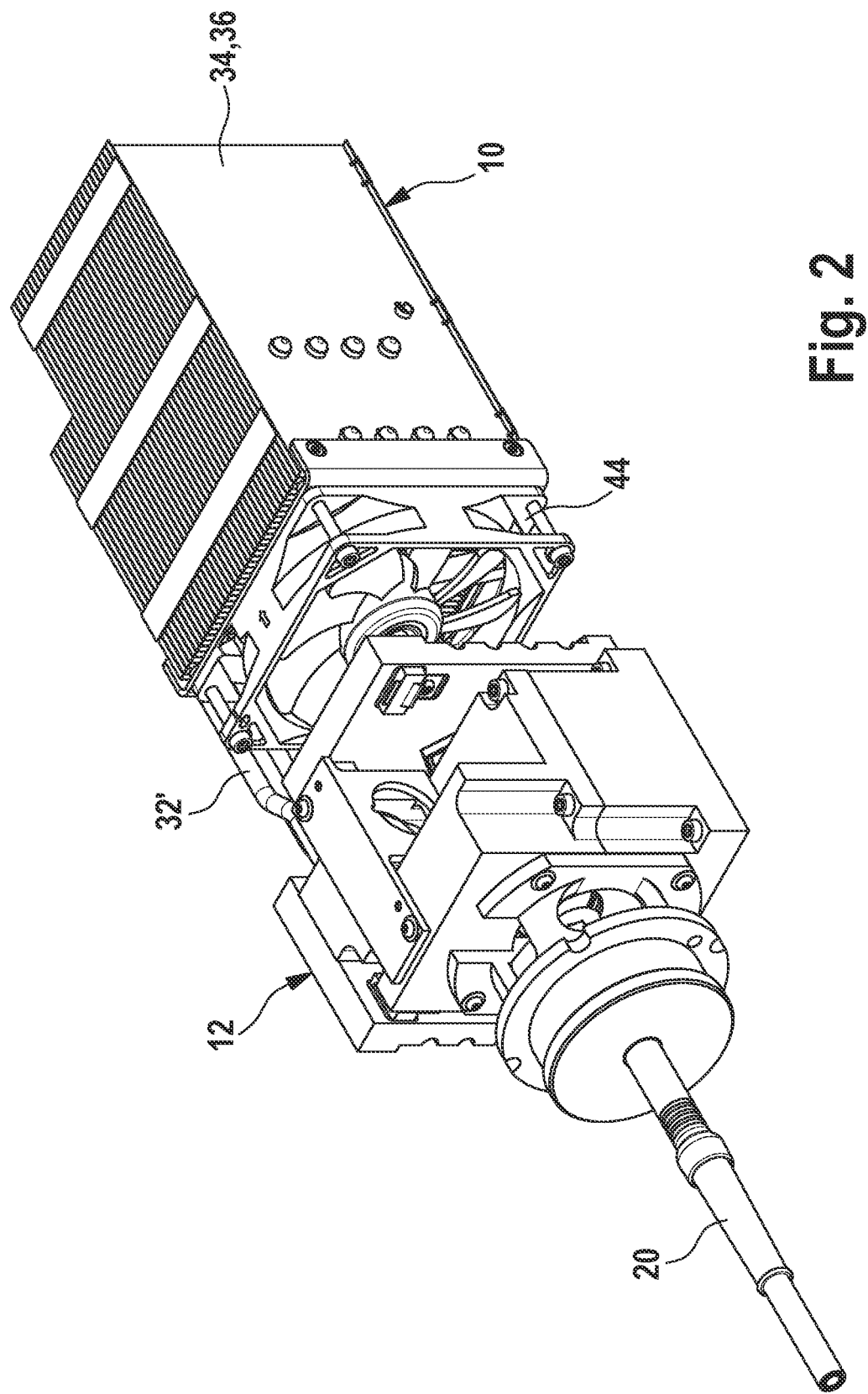
FIG. 2 is a perspective view of the refinement of the device.
Figure 3:
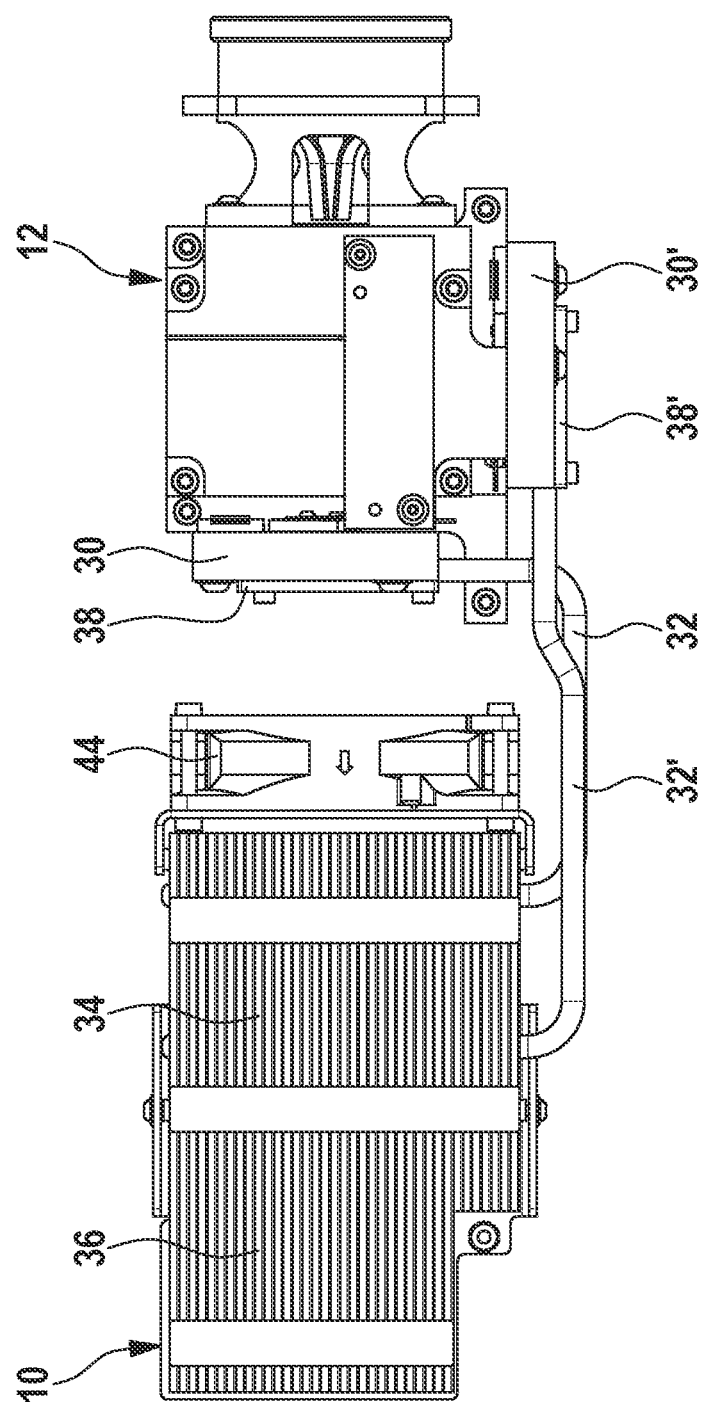
FIG. 3 is a top view of the refinement shown in FIG. 2.

For a better overview, FIGS. 2 and 3 again show the device 10 together with the optical unit 12 in an insulated form, i.e. without the remaining components of the endoscopic lighting apparatus 100 shown in FIG. 1.

Figure 4:
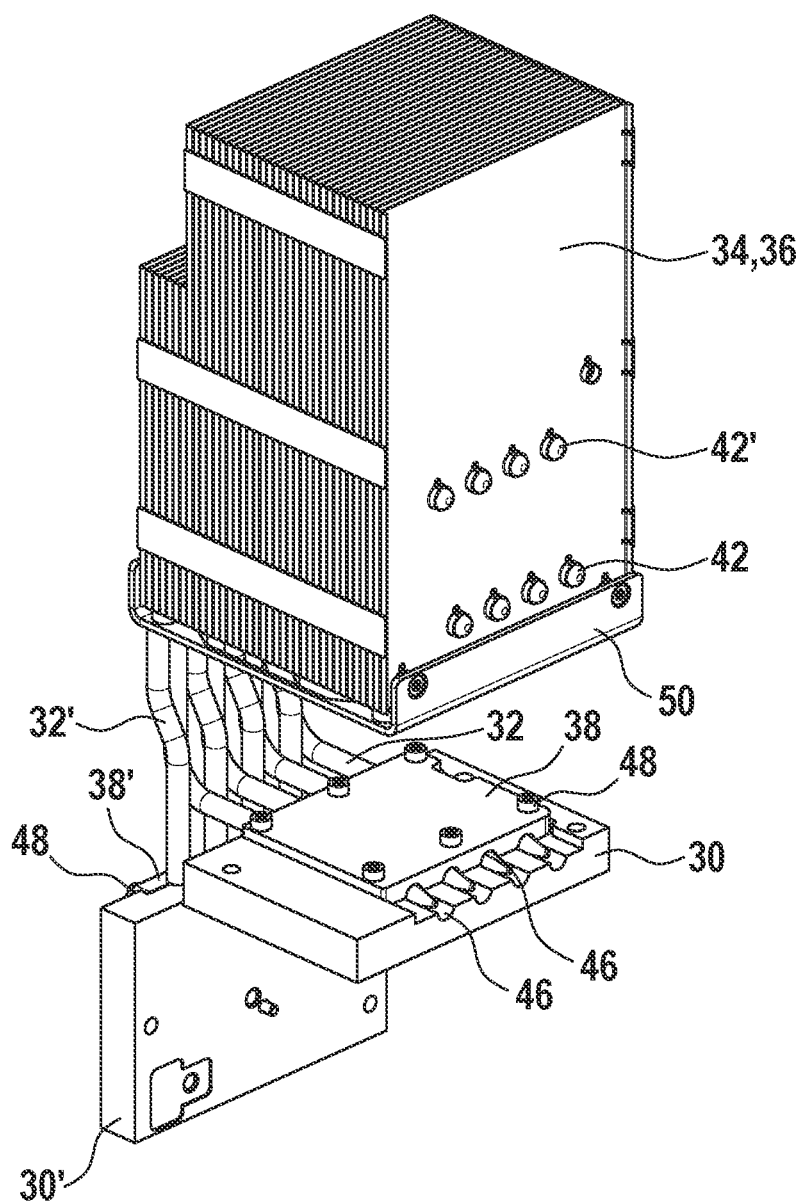
FIG. 4 is a perspective view of a second refinement of the device.
Figure 5:
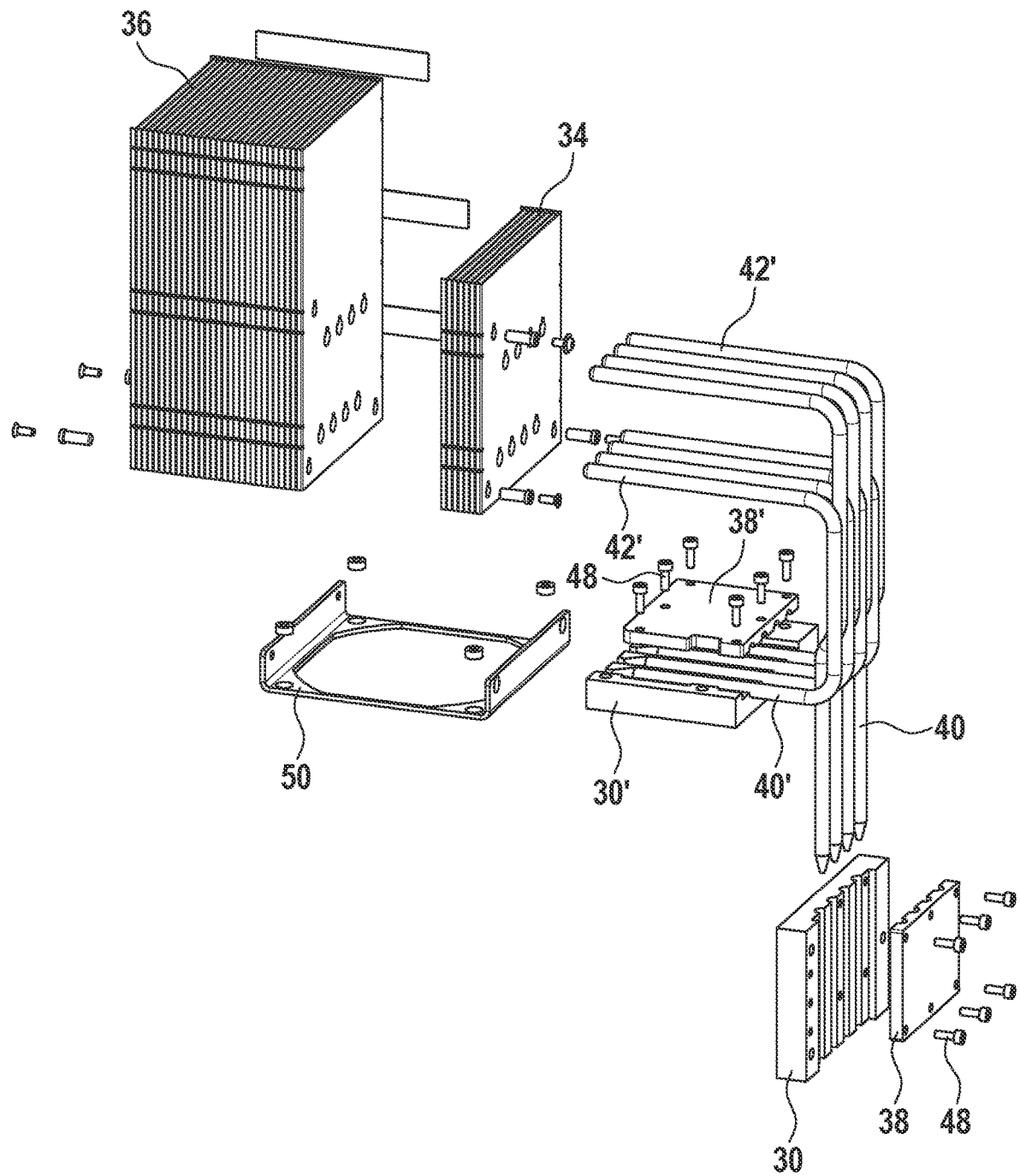
FIG. 5 is an exploded view of the second refinement.

FIGS. 4 and 5 show the device 10 as a refinement in a perspective view (FIG. 4) and in an exploded view (FIG. 5). In FIG. 4 it can be seen that both the first heat pipe 32 and the second heat pipe 32' each comprise a plurality (in the present case, each four) of heat conducting tubes, which are led from the first and second heat dissipation element 30, 30' to the heat sink 36 and which both end in the latter. The respective second end regions 42, 42' of the first and second heat pipe 32, 32' end in the heat sink 36 and, in the present case, penetrate it completely when viewed in a transverse direction of the heat sink 36.

The heat dissipation elements 30, 30' may each be plate-shaped and comprise several recesses 46. The clamping elements 38, 38' may comprise the same number of recesses 46 as the heat dissipation elements 30, 30'. Thus, the first end region 40 of the first heat pipe 32 can be enclosed by the first heat dissipation element 30 and the first clamping element 38. The first end region 40' of the second heat pipe 32' may be enclosed by the second heat dissipation element 30' and the second clamping element 38'. In some exemplary embodiments, the first and/or second heat pipes 32, 32' may be tubular.

In FIG. 4, the clamping elements 38, 38' are each attached to the respective heat dissipation element 30, 30' by several screws 48. In other refinements, the clamping elements 38, 38' may also be attached to the heat dissipation elements 30, 30', for example by bolts.

In the exploded view of the device 10 in FIG. 5, it can be seen that the respective first end regions 40, 40' as well as the respective second end regions 42, 42' of the first and second heat pipe 32, 32' run in a straight line and are tapered at an outer end of the conical shaped heat pipe, respectively.

The two heat dissipation elements 30, 30' may be mounted to the optical unit 12 with several bolts 52 (not shown here). A fan mounting frame 50 may be mounted, e.g. using several screws, on the heat sink 36, which fan mounting frame 50 is adapted to provide a mounting platform for the fan 44.

A heat-conducting paste for thermal coupling may also be applied between a surface of the first heat dissipation element 30, a surface of the first end region 40 of the first heat pipe 32 and a surface of the first clamping element 38. In other configurations, one or more heat-conducting pads and/or heat-conducting paste may be applied between the light sources 18, 18' and the heat dissipating elements 30, 30'.

Figure 6:
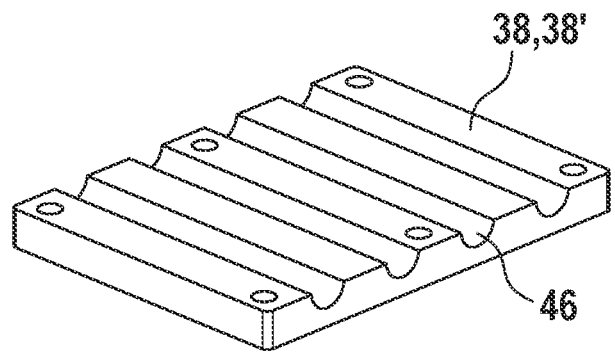
FIG. 6 is a perspective view of a first refinement of the clamping element.
Figure 7:
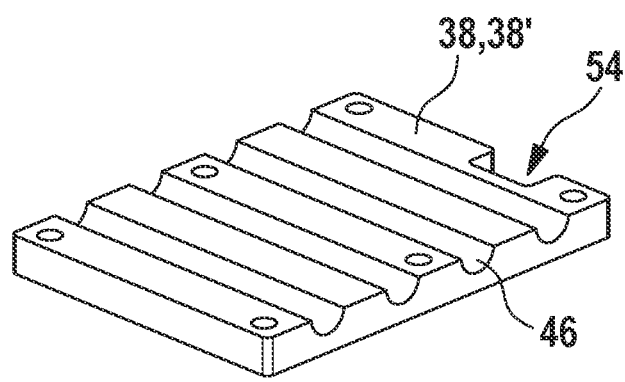
FIG. 7 is a perspective view of a second refinement of the clamping element.

FIGS. 6 and 7 show two refinements of the clamping element 38, 38', wherein the clamping element 38 shown in FIG. 6 differs from the clamping element 38' shown in FIG. 7 in that it comprises an additional notch 54 on one side of its rectangular outer edge. The notch 54 has no functional advantage but is of a purely constructive nature. As can be seen in FIGS. 6 and 7, the rectangular body of the clamping elements 38, 38' is traversed in a transverse direction by the several semi-cylindrical recesses 46.

Figure 8:
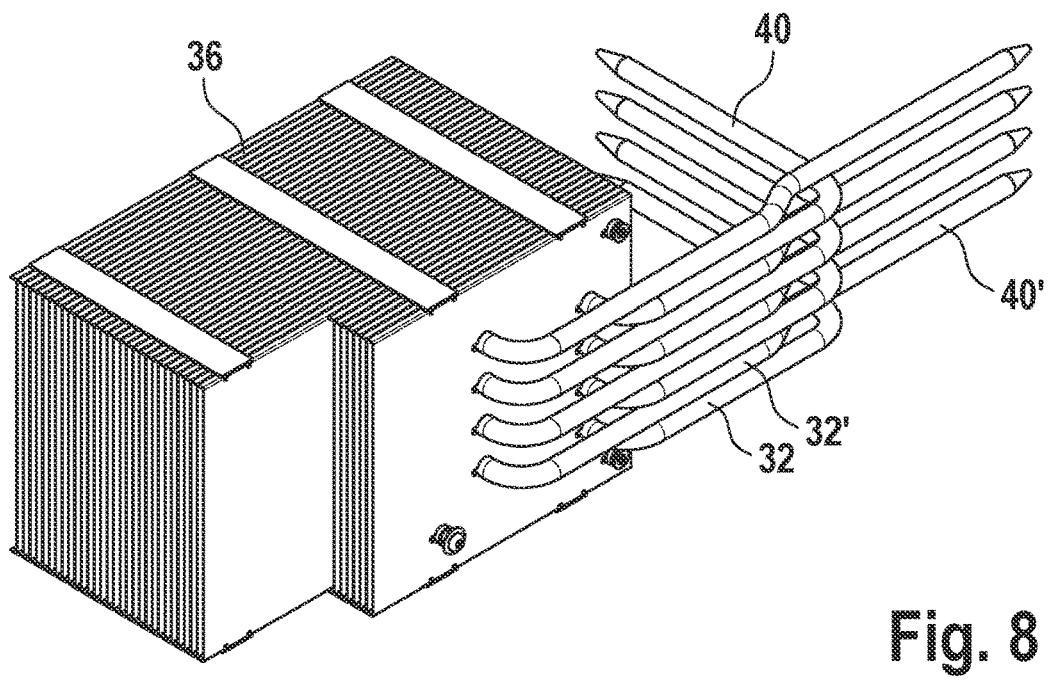
FIG. 8 is a perspective view of heat pipes and heat sink in the soldered state.
Figure 9:
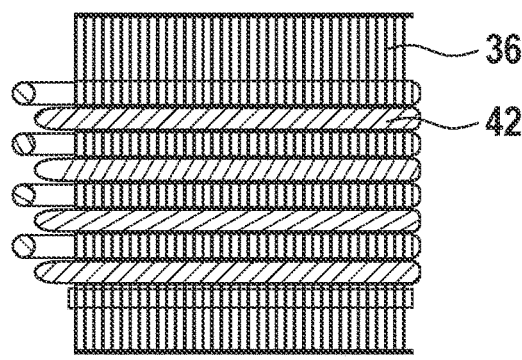
FIG. 9 is a sectional view of the perspective view shown in FIG. 8.

FIG. 8 shows a perspective view of the heat pipes 32, 32' in a state where the heat pipes 32, 32' are soldered to the heat sink 36. It can be seen that the first end regions 40, 40' of the heat pipes 32, 32' are exposed, i.e. not clamped with the heat dissipation elements 30, 30' and the clamping elements 38. FIG. 9 shows a sectional view of FIG. 8. It can be seen that the heat pipes 32, 32' penetrate the cooling body 36 in a transverse direction and are soldered to it.

Figure 10:
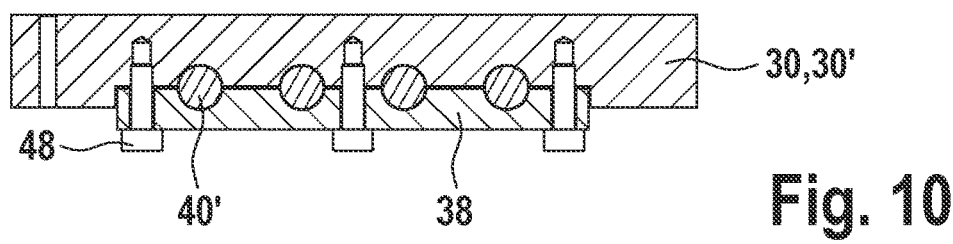
FIG. 10 is a sectional view of the heat pipe(s) in the clamped state.

FIG. 10 shows another sectional view of the heat pipes 32, 32' in a clamped/screwed state. Here, the heat pipes 32, 32' are clamped between the heat dissipation element 30, 30' and the clamping element 38. In the present case, the clamping is done by screwing via the screws 48.

What is claimed is:

1. A heat dissipating device configured to dissipate heat from an endoscopic illumination device comprising:
   one or more heat pipes each including a first end portion and a second end portion;
   a heat dissipation element configured to dissipate thermal energy from a first heat source associated with the endoscopic illumination device;
   a heat sink; and
   a clamp,
   wherein the clamp is reversibly detachably mounted on the heat dissipation element such that the first end portions of the one or more heat pipes are held between the heat dissipation element and the clamp,
   wherein the one or more heat pipes are adapted to conduct the thermal energy of the first heat source to the heat sink, and
   wherein the second end portion of the one or more heat pipes ends in the heat sink.

2. The heat dissipating device of claim 1, wherein the heat source is one or more lights.

3. The heat dissipating device of claim 2, wherein the one or more lights are one or more LEDs.

4. The heat dissipating device of claim 1, wherein the clamp is detachably screwed, pinned or bolted to the heat dissipation element.

5. The heat dissipating device of claim 1, wherein the one or more heat pipes, the heat dissipation element and the clamp include a thermally conductive material.

6. The heat dissipating device of claim 5, wherein the thermally conductive material includes one or more of aluminum and/or copper.

7. The heat dissipating device of claim 1, wherein a thermal coupling heat-conducting paste is applied between a surface of the heat-dissipating element, a surface of the first end region of the one or more heat pipes and a surface of the clamp.

8. The heat dissipating device of claim 1, further comprising one or more second heat pipes, a second heat dissipating element, a second clamp, and a second heat source associated with the endoscopic illumination device,
   the one or more second heat pipes each having a first end portion and a second end portion,
   wherein the second heat dissipation element is configured to dissipate thermal energy from the second heat source, wherein the second clamp is reversibly detachably mounted on the second heat dissipation element such that the first end portion of the one or more second heat pipes are held between the second heat dissipation element and the second clamp, wherein the one or more second heat pipes are adapted to conduct the thermal energy of the second heat source to the heat sink, and wherein the second end portion of the one or more second heat pipes ends in the heat sink.

9. The heat dissipating device of claim 8, wherein the second heat source is a second light.

10. The heat dissipating device of claim 9, wherein the second light is one or more LEDs.

11. The heat dissipating device of claim 8, wherein the second clamp is detachably screwed, pinned or bolted to the heat dissipation element.

12. The heat dissipating device of claim 8, wherein the heat pipe, the heat dissipation element and the clamping element include a thermally conductive material.

13. The heat dissipating device of claim 12, wherein the thermally conductive material includes one or more of aluminum and/or copper.

14. The heat dissipating device of claim 8, wherein a heat-conducting paste is applied between a surface of the second heat-dissipating element, a surface of the first end region of the one or more second heat pipes and a surface of the second clamp.

15. The heat dissipating device of claim 1, further comprising one or more second heat pipes, a second clamp, and a second heat source,
the one or more second heat pipes each having a first end portion and a second end portion,
wherein the heat dissipation element is further configured to dissipate thermal energy from the second heat source associated with the endoscopic illumination device,
wherein the second clamp is reversibly releasably mounted on the heat dissipation element such that the first end portion of the one or more second heat pipes is held between the heat dissipation element and the second clamp, wherein the one or more second heat pipes are adapted to conduct the thermal energy of the second heat source to the heat sink, wherein the second end portion of the one or more second heat pipes ends in the heat sink.

16. The heat dissipating device of claim 15, wherein the second heat source is a second light.

17. The heat dissipating device of claim 16, wherein the second light is one or more LEDs.

18. The heat dissipating device of claim 15, wherein the second clamp is detachably screwed, pinned or bolted to the heat dissipation element.

19. The heat dissipating device of claim 1, further comprising:
a cooling body forming the heat sink of the device; and
a fan adapted to force an air flow over the heat sink.

20. The heat dissipating device of claim 1, wherein the heat dissipation element and the clamp include one or more complementary semi-cylindrical recesses adapted to receive one of the one or more heat pipes.

21. The heat dissipating device of claim 1, further comprising:
one or more second heat pipes each including a first end portion and a second end portion;
a second heat dissipation element; and
a second clamp, wherein:
the heat dissipation element and the clamp are located on a first plane, and the second heat dissipation element and the second clamp are located on a second plane perpendicular to the first plane.

22. The heat dissipating device of claim 21, wherein there are a plurality of heat pipes and a plurality of second heat pipes, and the plurality of heat pipes are arranged in a parallel configuration, and the plurality of second heat pipes are arranged in a parallel configuration.

23. A heat dissipating device configured to dissipate heat from an endoscopic illumination device comprising:
a plurality of first heat pipes each including a first end portion and a second end portion;
a plurality of second heat pipes each including a first end portion and a second end portion;
a first heat dissipation element and a first clamp configured to dissipate thermal energy from a first heat source associated with the endoscopic illumination device;
a second heat dissipation element and a second clamp also configured to dissipate thermal energy from the first heat source; and
a heat sink connected by the plurality of first heat pipes and the plurality of second heat pipes to the first heat dissipation element and the first clamp, and the second heat dissipation element and the second clamp, respectively,
wherein the clamps are detachably mounted on their respective heat dissipation elements such that the first end portions of the plurality of first heat pipes are held between the first heat dissipation element and the first clamp, and the first end portions of the plurality of second heat pipes are held between the second heat dissipation element and the second clamp,
wherein the plurality of heat pipes are adapted to conduct the thermal energy from the first heat source to the heat sink, and
wherein the second end portions of the first and the second plurality of heat pipes are located in the heat sink.

* * * * *